United States Patent
Mundla

(10) Patent No.: US 7,872,020 B2
(45) Date of Patent: Jan. 18, 2011

(54) TGF-β INHIBITORS

(75) Inventor: Sreenivasa Reddy Mundla, Westfield, IN (US)

(73) Assignee: Eli Lilly and Company, Indianapolis, IN (US)

(*) Notice: Subject to any disclaimer, the term of this patent is extended or adjusted under 35 U.S.C. 154(b) by 385 days.

(21) Appl. No.: 11/995,938

(22) PCT Filed: Jun. 29, 2006

(86) PCT No.: PCT/US2006/025377

§ 371 (c)(1),
(2), (4) Date: Jan. 17, 2008

(87) PCT Pub. No.: WO2007/018818

PCT Pub. Date: Feb. 15, 2007

(65) Prior Publication Data

US 2010/0120854 A1    May 13, 2010

Related U.S. Application Data

(60) Provisional application No. 60/701,641, filed on Jul. 22, 2005.

(51) Int. Cl.
*A01N 43/00* (2006.01)
*A61K 31/33* (2006.01)

(52) U.S. Cl. .................................................. 514/314

(58) Field of Classification Search ............. 430/58.55; 534/636; 514/404

See application file for complete search history.

(56) References Cited

FOREIGN PATENT DOCUMENTS

| WO | WO 02/094833 | 11/2002 |
|---|---|---|
| WO | WO 2004/048382 | 6/2004 |
| WO | WO 2004/048383 | 6/2004 |

OTHER PUBLICATIONS

IMPCA methanol reference specifications.*

* cited by examiner

*Primary Examiner*—Brandon J Fetterolf
*Assistant Examiner*—Jean Cornet
(74) *Attorney, Agent, or Firm*—Elizabeth A. McGraw; Danica Hostettler; Tina M. Tucker

(57) ABSTRACT

The present invention provides crystalline 2-(6-methyl-pyridin-2-yl)-3-[6-amido-quinolin-4-yl)-5,6-dihydro -4H-pyrrolo[1,2-b]pyrazole monohydrate.

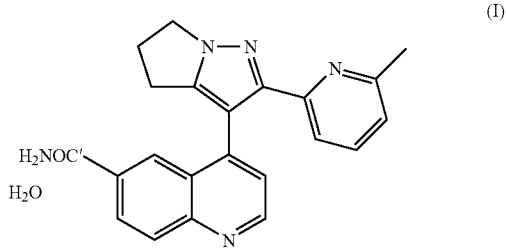

4 Claims, No Drawings

TGF-β INHIBITORS

This application is a 35 U.S.C. 371 National Stage Filing of PCT/US2006/025377 filed Jun. 29, 2006, which claims priority to U.S. Provisional Application No. 60/701,641, filed Jul. 22, 2005.

BACKGROUND OF THE INVENTION

Transforming growth factor-beta (TGF-β) is a prototype for a large family of growth and differentiation factors that regulate development. TGF-β family members activate transmembrane serine/threonine receptor kinases, thereby initiating a signaling cascade via Smads, a novel class of intracellular signaling effectors that regulate gene expression. TGF-β is a potent inducer of growth arrest in many cell types, including epithelial cells. This activity is the basis of the tumor suppressor role of the TGF-β signaling system in carcinomas. Other activities, including TGF-β-induced epithelial-to-mesenchymal differentiation, contribute to cancer progression.

TGF-β family signaling is of special relevance in mesenchymal differentiation, including bone development. Deregulated expression or activation of components of this signaling system can contribute to skeletal diseases, e.g. osteoarthritis. See Wakefield, et al. (2002) Current Opinion in Genetics & Development 12:22-29; Siegel, et al. (2003) Nature Reviews (Cancer) 3:807-820; Dumont, et al. (2003) Cancer Cell 3:531-536.

PCT patent application WO 02/0948332 describes a genus of dihydropyrrolopyrazole compounds useful for treating disorders associated with enhanced TGF-β signaling activity or overproduction. PCT patent application WO 04/04382 describes an anhydrous form of 2-(6-methyl-pyridin-2-yl)-3-[6-amido-quinolin-4-yl)-5,6-dihydro -4H-pyrrolo[1,2-b]pyrazole.

It has been surprisingly discovered that 2-(6-methyl-pyridin-2-yl)-3-[6-amido-quinolin -4-yl)-5,6-dihydro-4H-pyrrolo[1,2-b]pyrazole can be prepared in a crystalline monohydrate form having the advantageous properties relative to the anhydrous form of superior solid handling properties on a large scale, ease of purification by crystallization, and thermodynamic stability under conditions of pharmaceutical processing and storage. A manufacturing process for the new form has also been discovered.

SUMMARY OF THE INVENTION

The present invention provides 2-(6-methyl-pyridin-2-yl)-3-[6-amido-quinolin-4-yl) -5,6-dihydro-4H-pyrrolo[1,2-b]pyrazole monohydrate, i.e., Formula I.

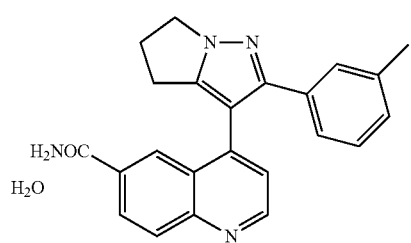

Formula I

The present invention provides 2-(6-methyl-pyridin-2-yl)-3-[6-amido-quinolin-4-yl) -5,6-dihydro-4H-pyrrolo[1,2-b]pyrazole monohydrate in a crystalline form.

The present invention provides a pharmaceutical composition comprising 2-(6-methyl-pyridin-2-yl)-3-[6-amido-quinolin-4-yl)-5,6-dihydro-4H-pyrrolo[1,2-b]pyrazole monohydrate and a pharmaceutically acceptable excipient, diluent or carrier.

The present invention provides a method of inhibiting TGF-β signaling in a mammal comprising administering to a mammal in need of such treatment an effective amount of 2-(6-methyl-pyridin-2-yl)-3-[6-amido-quinolin-4-yl)-5,6-dihydro-4H -pyrrolo[1,2-b]pyrazole monohydrate.

The present invention further provides a method of treating conditions resulting from excessive TGF-β production in a mammal comprising administering to a mammal in need of such treatment a TGF-β signal-suppressing amount of 2-(6-methyl-pyridin-2-yl) -3-[6-amido-quinolin-4-yl)-5,6-dihydro-4H-pyrrolo[1,2-b]pyrazole monohydrate.

Because the compounds of the present invention are inhibitors of TGF-β signaling, the compounds of the present invention are useful for the treatment of a variety of disorders including the treatment of susceptible neoplasms.

In one of its method aspects, this invention is directed to a method for treating susceptible neoplasms comprising administering to a patient in need thereof an effective amount of 2-(6-methyl-pyridin-2-yl)-3-[6-amido-quinolin-4-yl)-5,6-dihydro-4H -pyrrolo[1,2-b]pyrazole monohydrate.

The present invention provides 2-(6-methyl-pyridin-2-yl)-3-[6-amido-quinolin-4-yl) -5,6-dihydro-4H-pyrrolo[1,2-b]pyrazole monohydrate for use in therapy. The present invention provides for the use of 2-(6-methyl-pyridin-2-yl)-3-[6-amido-quinolin-4-yl) -5,6-dihydro-4H-pyrrolo[1,2-b]pyrazole monohydrate for the manufacture of a medicament for the treatment of disorders associated with enhanced TGF-β signaling activity or overproduction.

In another embodiment this invention provides a process for making 2-(6-methyl-pyridin-2-yl) -3-[6-amido-quinolin-4-yl-5,6-dihydro-4H-pyrrolo[1,2-b]pyrazole monohydrate and novel intermediates useful for making crystalline 2-(6-methyl-pyridin-2-yl) -3-[6-amido-quinolin-4-yl)-5,6-dihydro-4H-pyrrolo[1,2-b]pyrazole monohydrate: 6-cyano-4-methyl-quinoline hydrochloride, 2-(6-cyano-quinolin-4-yl)-1-(6-methyl-pyridin-2-yl)-ethanone; 1-amino)-2-pyrrolidinone, p-toluene sulfonate; 1-[(6-methyl-pyridin-2-yl) -2-(6-cyano-quinolin-4-yl)-ethylideneamino]-pyrrolidin-2-one; and 3-(6-cyano-quinolin-4-yl) -2-(6-methyl-pyridin-2-yl)-5,6-dihydro-4H-pyrrolo[1,2-b]pyrazole.

DETAILED DESCRIPTION OF THE INVENTION

As used herein, the term "6-cyano-4-methyl-quinoline hydrochloride" refers to

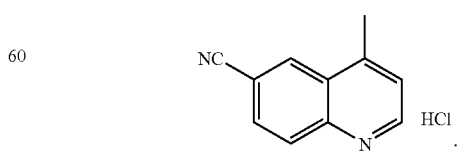

The term "2-(6-cyano-quinolin-4-yl)-1-(6-methyl-pyridin-2-yl)-ethanone" refers to

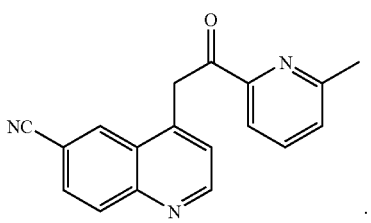

The term "1-amino)-2-pyrrolidinone, p-toluene sulfonate" refers to

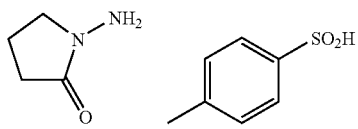

The term "1-[(6-methyl-pyridin-2-yl)-2-(6-cyano-quinolin-4-yl)-ethylideneamino]-pyrrolidin-2-one" refers to

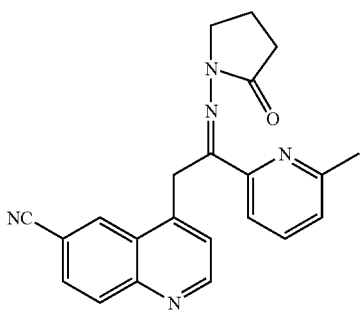

The term "3-(6-cyano-quinolin-4-yl)-2-(6-methyl-pyridin-2-yl)-5,6-dihydro-4H -pyrrolo[1,2-b]pyrazole" refers to

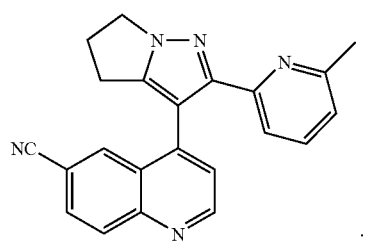

The term "effective amount" of a compound of the present invention refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of the present invention, a number of factors are considered by the attending diagnostician, including, but not limited to: the compound of the present invention to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of the present invention is expected to be delivered QD or BID at 10 mg to 1 g total daily dose, preferably from 100-200 mg preferred flat dose. An effective amount could also be once a day or once a week dosing with sustained release formulations. More preferred amounts can be determined by one skilled in the art.

It is understood that TGF-β includes both TGF-β1 and TGF-β2.

Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless-of the cause.

There are several types of cancer, i.e., susceptible neoplasms, where TGF-β1 produced by the tumor may be deleterious. These include prostrate cancer (e.g., Steiner and Barrack (1992) Mol. Endocrinol 6:15-25), colorectal cancer (e.g., Neurath et al. (2004) Immunity. 21:491-501), breast cancer (e.g., Arteaga, et al. (1993) Cell Growth and Differ. 4:193-201), non-small cell lung cancer (e.g., Ready et al., (April 2005) Semin Oncol. 32(2 Suppl 3):S35-41, ovarian cancer (e.g., Dr. Gustavo C. Rodriguez, (Mar. 2-7, 2001) 32nd Annual Meeting of the Society of Gynecologic Oncologists. Nashville, Tenn.), endometrial cancer (e.g., Dowdy et al, (February 2005) Gynecol Oncol. 96(2):368-73), testicular cancer (e.g., Morera et al., (1992) Endocrinology. 130:831-836), osteosarcoma (e.g., Kloen et al., (Aug. 1, 1994) Int J Cancer. 58(3):440-5), and multiple myeloma (e.g., Cook et al., (1999) Journal of Leukocyte Biology, Vol 66, Issue 6:981-988). See also PCT patent application WO 02/0948332.

Another embodiment of the present invention is the crystalline monohydrate form of 2-(6-methyl-pyridin-2-yl)-3-[6-amido-quinolin-4-yl)-5,6-dihydro-4H-pyrrolo[1,2-b]pyrazole. This compound has been characterized as described below.

X-Ray Powder Diffraction

The X-ray powder diffraction (XRD) pattern of the crystalline monohydrate was obtained on a Siemens D5000 X-ray powder diffractometer, equipped with a CuKα source (λ=1.54056 Å) and a Kevex solid state Si(Li) detector, operating at 50 kV and 40 mA. Each sample was scanned between 3 and 40 in 2θ, with a step size of 0.02° in 2θ and a scan rate of 9.0 seconds/step, and with 1 mm divergence and receiving slits and a 0.1 mm detector slit. The dry powder was packed into recessed top-loading sample holder and a smooth surface was obtained using a glass slide. The monohydrate crystal form diffraction pattern, collected at ambient temperature and relative humidity, was adjusted based on the NIST 675 standard peak at 8.85 degrees 2-theta.

| Angle (+/−0.01 degrees) | d-spacing |
|---|---|
| 9.05 | 9.76 |
| 10.25 | 8.63 |
| 11.02 | 8.02 |
| 11.95 | 7.40 |
| 12.37 | 7.15 |
| 13.49 | 6.56 |
| 14.84 | 5.96 |
| 17.48 | 5.07 |
| 20.11 | 4.41 |
| 20.77 | 4.27 |
| 24.13 | 3.69 |
| 25.38 | 3.51 |
| 26.00 | 3.42 |
| 26.73 | 3.33 |
| 28.79 | 3.10 |
| 29.91 | 2.98 |
| 31.84 | 2.81 |

Thus, a properly prepared sample of 2-(6-methyl-pyridin-2-yl)-3-[6-amido-quinolin -4-yl-5,6-dihydro-4H-pyrrolo[1,2-b]pyrazole monohydrate may be characterized by X-ray diffraction pattern using CuK$_\alpha$ radiation as having diffraction peaks (2-theta values) as described in Table 1, and in particular having peaks at 9.05 in combination with one or more of the peaks at 11.02, 11.95, and 14.84; and more particularly having a peak at 9.05; with a tolerance for the diffraction angles of 0.1 degrees, more preferably 0.01 degrees.

Solid-State $^{13}$C NMR Spectroscopy $^{13}$C Cross polarization/magic angle spinning (CP/MAS) NMR (solid-state NMR or SSNMR) spectra were obtained for the crystalline monohydrate using a Varian Unity Inova 400 MHz NMR spectrometer operating at a carbon frequency of 100.573 MHz and equipped with a complete solids accessory and a Chemagnetics 4.0 mm T3 probe. Ramped-amplitude cross-polarization (RAMP-CP) at 62 kHz and two-pulse phase modulation (TPPM) decoupling at 70 kHz were used. Acquisition parameters were as follows: 90° proton radio frequency pulse width 4.0 μs, contact time 2.0 ms, pulse repetition time 60 s, MAS frequency 10 kHz, spectral width 50 kHz, and acquisition time 50 ms. Chemical shifts were referenced to the methyl group of hexamethylbenzene (δ=17.3 ppm) by sample replacement.

$^{13}$C chemical shifts of monohydrate crystal form: 20.5, 22.5, 26.3, 48.7, 108.8, 115.6, 122.6, 127.9, 128.8, 130.5, 136.4, 146.8, 149.0, 151.3, 152.0, 153.2, 157.9, and 171.0 (+/−0.2) ppm.

Thus, crystalline 2-(6-methyl-pyridin-2-yl)-3-[6-amido-quinolin-4-yl-5,6-dihydro -4H-pyrrolo[1,2-b]pyrazole monohydrate may be characterized by solid state $^{13}$C nuclear magnetic resonance having chemical shift (ppm) of 108.8, 115.6, 122.6, and 171.0 (+/−0.2) ppm.

In another embodiment this invention provides a process for preparing 2-(6-methyl-pyridin-2-yl) -3-[6-amido-quinolin-4-yl-5,6-dihydro-4H-pyrrolo[1,2-b]pyrazole monohydrate comprising crystallizing 2-(6-methyl-pyridin-2-yl)-3-[6-amido-quinolin-4-yl-5, 6-dihydro-4H-pyrrolo[1,2-b]pyrazole from an appropriate solvent containing an organic solvent to water ratio of 0-90% under conditions which yield 2-(6-methyl-pyridin-2-yl) -3-[6-amido-quinolin-4-yl-5,6-dihydro-4H-pyrrolo[1,2-b]pyrazole monohydrate.

2-(6-methyl-pyridin-2-yl)-3-[6-amido-quinolin-4-yl-5,6-dihydro-4H-pyrrolo[1,2-b]pyrazole monohydrate may be prepared by crystallization under controlled conditions. In particular, the monohydrate of the present invention can be prepared by crystallization from an aqueous solvent. A suitable solvent is one that has an organic solvent to water ratio of 0-90% organic solvent. Preferred is an organic solvent to water ratio between 60:40 to 85:15. More preferred is an organic solvent to water ratio of 75:25. Preferred organic solvents are acetonitrile, acetone, tetrahydrafuran (THF), methyl ethyl ketone, dimethyl sulfoxide (DMSO), dimethyl formamide (DMF), N,N-dimethyl acetamide, and N-methyl pyrrolidinone. In practice, it has been found that acetone is most preferred. After suspending anhydrous, monohydrated, or partially hydrated 2-(6-methyl-pyridin-2-yl) -3-[6-amido-quinolin-4-yl-5,6-dihydro-4H-pyrrolo[1,2-b]pyrazole in a suitable solvent, the mixture is stirred at 20 to 100° C., preferably 60° C. For lower boiling point solvents such as acetonitrile, acetone, and methyl ethyl ketone, the volume of the resulting solution is reduced, preferably by distillation, to between 35-70% of the initial volume, preferably 50%. For higher boiling point solvents, an appropriate amount of additional water may need to be added to precipitate the product. During the reduction, seed crystals of monohydrate may be added. Slowly cool the solution to 0-5° C., preferably in two stages wherein the solution is first cooled to 20-25° C. over 90 minutes followed by cooling to 0-5° C. over 30-40 minutes. Hold the slurry at 0-5° C. for an additional 30 minutes to 25 hours, preferably 2-3 hours. Filter the slurry and rinse the product, preferably with water or aqueous organic solvent. Dry the product, preferably at 45° C.

In another embodiment 2-(6-methyl-pyridin-2-yl)-3-[6-amido-quinolin-4-yl)-5,6-dihydro -4H-pyrrolo[1,2-b]pyrazole monohydrate can be prepared by reslurrying 2-(6-methyl-pyridin -2-yl)-3-[6-amido-quinolin-4-yl)-5,6-dihydro-4H-pyrrolo[1,2-b]pyrazole in water or aqueous DMSO.

2-(6-Methyl-pyridin-2-yl)-3-[6-amido-quinolin-4-yl-5,6-dihydro-4H-pyrrolo[1,2-b]pyrazole monohydrate may be prepared by stirring in 10 volumes of 0-90% organic solvent to water at room temperature for 1-2 hours, filtering, and drying at 35-45° C., preferably 45° C. under vacuum. In cases where organic solvent is used, the reaction mixture may be diluted with water (2-5 times the volume of organic solvent used) to improve recovery.

Crystalline 2-(6-methyl-pyridin-2-yl)-3-[6-amido-quinolin-4-yl)-5,6-dihydro-4H-pyrrolo [1,2-b]pyrazole monohydrate can be prepared by a variety of procedures, some of which are illustrated in the examples below: It will be recognized by one of skill in the art that the order of the individual steps in the following may be varied to provide crystalline 2-(6-methyl-pyridin-2-yl)-3-[6-amido-quinolin-4-yl)-5,6-dihydro-4H -pyrrolo[1,2-b]pyrazole monohydrate:

Preparation 1

Preparation of 2-(6-methyl-pyridin-2-yl)-3-[6-amido-quinolin-4-yl)-5,6-dihydro-4H -pyrrolo[1,2-b] pyrazole monohydrate seed crystals To a flask equipped with mechanical stirrer add 3-(6-cyano-quinolin-4-yl)-2-(6-methyl-pyridin-2-yl) -5,6-dihydro-4H-pyrrolo[1,2-b]pyrazole (500.2 g), potassium carbonate (39.4 g), and DMSO (3,000 mL) to form a slurry. In a separate flask, combine 35% hydrogen peroxide (154 mL) and deionized water (250 mL). Add the dilute hydrogen peroxide solution to the above slurry over 30 to 45 minutes in such a way that the reaction temperature is in the range of 22 to 34° C. After completion of addition, stir the reaction mixture until the reaction is complete as judged by HPLC.

Prepare a solution of sodium sulfite (107.6 g) in deionized water (4,500 mL). Add the reaction mixture slowly to the sodium sulfite solution to quench the reaction solution while maintaining the temperature from 22 to 40° C. Stir the reaction mixture for 40-60 minutes and add concentrated (37.5%) HCl acid (450 mL). To the resulting solution add activated charcoal (56.4 g) and stir for 10-15 minutes. Filter the solution through diatomaceous earth to remove the activated charcoal. Add methanol (525 mL) to the filtrate and then add sodium hydroxide (1,700 mL) over 35 minutes. Stir the resulting slurry overnight and filter.

Suspend the wet cake in a 66.75% acetonitrile in water solution (10,000 mL). Heat the resulting mixture to reflux (~77 to 81° C.) and stir for 20 minutes. Cool the mixture to 40° C. and add deionized water (2,500 mL) and then cool to 0-5° C. and stir for 2 to 3 hours. Filter the slurry wash the cake with deionized water (500 mL). Dry the cake overnight at 40° C. in a vacuum oven to furnish 404.2 g of product.

Preparation 2

Preparation of 2-(6-cyano-quinolin-4-yl)-1-(6-methyl-pyridin-2-yl)-ethanone seed crystals To a flask equipped with an N$_2$ purge and overhead stirring, charge 6-cyano-6-methyl quinoline hydrochloride (10 g, 1 equiv) and THF (100 mL, 10 vol), then cool the mixture to 20-25° C. Add NaOt-bu (15.497 g, 3.3 equiv) in portions over 30 minutes to control the exotherm, keeping the temperature ≦25° C. Then add a solution of methyl-6-methyl pyridine-2-carboxylate (11.08 g, 1.5 equiv) in THF (20 mL, 2 vol) dropwise to keep the temperature between 20° C. and 25° C. Monitor reaction completion by HPLC analysis (~2 h). Once complete, cool the mixture to below 15° C. and add 1 N HCl (70 mL). Adjust pH to 8.0-9.0 with 5N NaOH (final pH at 8.8). Add EtOAc (70 mL) and separate the aqueous layer and wash the organic layer with saturated aqueous sodium chloride (35 mL) and saturated bicarbonate (35 mL). Concentrate the organic layer in vacuo to ~5 vol and slowly add MeOH (10 vol), then distill off 10 vol and add back MeOH (10 vol). Cool the mixture to 5° C., filter and rinse the cake with MeOH (5 vol), then dry the cake in vacuo at 40° C. to furnish 11.5 g of product.

EXAMPLE 1

Preparation of 2-(6-methyl-pyridin-2-yl)-3-[6-amido-quinolin-4-yl-5,6-dihydro-4H -pyrrolo[1,2-b] pyrazole monohydrate

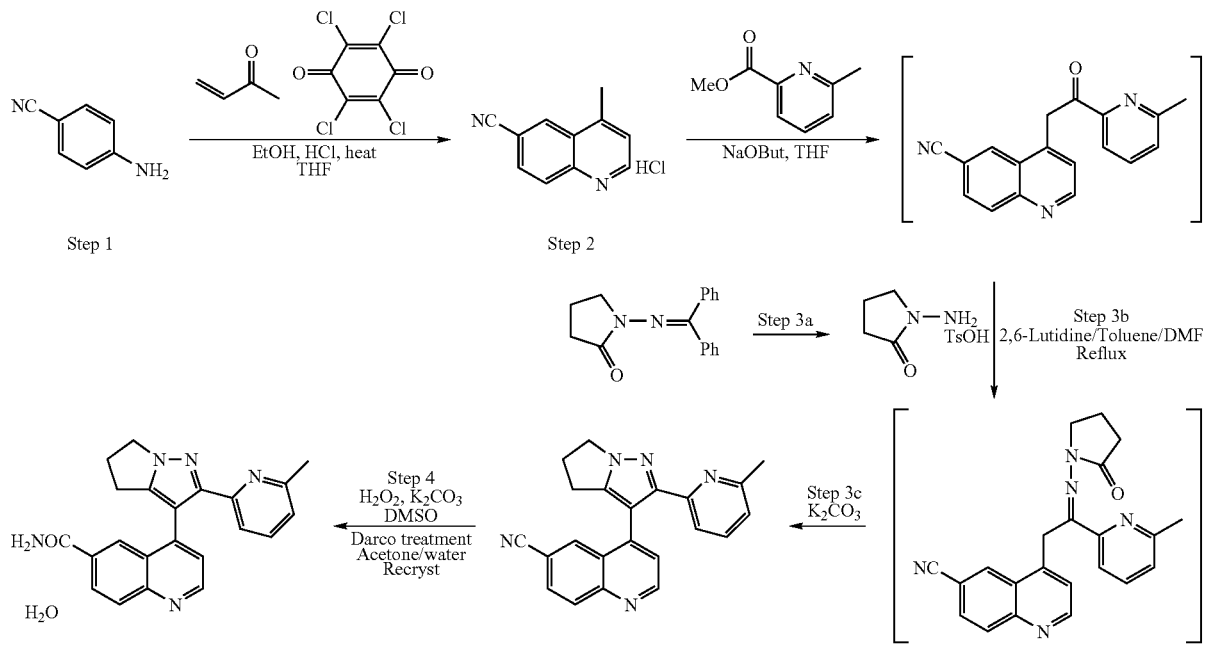

Step 1: Preparation of 6-cyano-4-methyl-quinoline hydrochloride

Add 95% ethanol (EtOH) (270 L, 9 vol.), 4-aminobenzonitrile (30.0 kg, 1 equiv) and 2,3,5,6-tetrachloro-2,5-cyclohexadiene-1,4-dione, (66.81 kg 1.07 equiv) to a 200 gallon reaction vessel equipped with nitrogen purge, condenser, thermocouple, and overhead agitation. Stir for 2-5 min, then add concentrated hydrochloric acid (HCl) (62.56 L, 3.0 equiv), then heat to 75° C. Dilute methyl vinylketone (33.06 L, 1.5 equiv) in 95% EtOH (30 L, 1 vol.) then add slowly to reaction mixture over 30 min. Monitor for reaction completion by high performance liquid chromatography (HPLC). Add tetrahydrofuran (THF) (11 vol., 330 L), at 75° C., then stir for 1 hour at 60° C. Cool to room temperature and stir for 1 additional hour. Filter on agitated filter/dryer, then rinse with THF (240 L, 8 volumes). Dry overnight under vacuum at 70° C. to give the title compound (42.9 kg, 82.55%).

$^1$H NMR (DMSO d6): δ=9.047 ppm (d, 4.4 Hz, 1H); 8.865 ppm (d, 1.6 Hz, 1H); 8.262 ppm (d, 8.8 Hz, 1H); 8.170 ppm (dd, 2.2 Hz, 8.8 Hz, 1H); 7.716 ppm (d, 4.4 Hz, 1H); 2.824 ppm (s, 3H). MS ES+: 169.1; Exact: 168.07.

Step 2: Preparation of 2-(6-cyano-quinolin-4-yl)-1-(6-methyl-pyridin-2-yl)-ethanone Combine the 6-cyano-4-methyl-quinoline (28 kg) and THF (9.5 vol.) and cool to 5° C. Add sodium t-butoxide solid (3.3 equiv.) in portions to the cooled slurry to keep the batch temperature ≦25° C. Stir the resulting mixture at 20° C. for 30 min. To a separate vessel, charge with liquid 6-methyl-2-pyridinecarboxylic acid, methyl ester (1.5 equiv.) and dilute with THF (2.0 vols.). The 6-methyl-2-pyridinecarboxylic acid, methyl ester solution is slowly added (20-40 min) while maintaining a temperature of ≦25° C. Stir the reaction mixture for 2 hours at 20° C. and monitor by HPLC/TLC (thin layer chromatography on silica gel) to confirm reaction completion. In a separate vessel, dilute 1.03 kg conc. HCl per kg of 2-(6-cyano-quinolin-4-yl)-1-(6-methyl-pyridin-2-yl)-ethanone with 7.7 vol water. Cool both the reaction mixture and the HCl solution to 5° C. Perform a pH adjustment on the reaction mixture by the slow addition of the acid solution, keeping the temperature <15° C. Acid solution is added until the pH of the mixture is 8.0-9.0. After the pH endpoint is obtained, extract the mixture with ethyl acetate (7 vol.). Wash the organic layer with an aqueous sodium chloride/sodium bicarbonate solution [0.78 kg sodium chloride per kg of 2-(6-cyano-quinolin-4-yl)-1-(6-methyl-pyridin-2-yl) -ethanone, and 0.20 kg of sodium bicarbonate (NaHCO$_3$) per kg of 2-(6-cyano-quinolin-4-yl)-1-(6-methyl-pyridin-2-yl)-ethanone in 6.6 vol.]. Distill the organic layer at one atmosphere to remove THF and ethylacetate (EA) until 5 vol. of concentrated solution remains. Using methanol (10 vol.) perform a solvent exchange to methanol using a constant add/distill operation while maintaining 5 vol. Add warm methanol (MeOH) (10 vol. @ 60° C.). Cool the solution to 50° C., then add seed crystals obtained by Preparation 2. Cool the mixture gradually to 5° C., stir for 1 hour, and filter. Wash the product cake with chilled methanol (5 vols. @ 5° C.) and dry under vacuum at 40° C. until a loss on drying (LOD) specification of <1% is satisfied. Gives the title compound (31.6 kg, 81%).

$^1$H NMR (CDCl$_3$): δ=8.978 ppm (d, 4.4 Hz, 1H); 8.627 ppm (d, 1.6 Hz, 1H); 8.199 ppm (d, 8.8 Hz, 1H); 7.874 ppm (d, 7.7 Hz, 1H); 7.837 ppm (dd, 2.2 Hz, 8.8 Hz, 1H); 7.759 ppm (t, 7.7 Hz, 1H); 7.546 ppm (d, 4.4 Hz, 1H); 7.416 ppm (d, 7.7 Hz, 1H); 5.036 ppm (s, 2H); 2.720 ppm (s, 3H). MS ES+: 288.1; Exact: 287.11.

Step 3a: Preparation of 1-(amino)-2-pyrrolidinone, p-toluene sulfonate

Combine 1-[(Diphenylmethylene)amino]-2-pyrrolidinone (35.36 g, 134 mmoles) with 15 volumes of toluene (530 mL) in a 1 L reaction flask, add 1 equiv of water (2.43 g, 134.9 mmoles) and heat to 40° C. Add 1 equiv of p-toluensulfonic acid monohydrate (25.978 g, 133.8 mmoles). Monitor reaction by TLC, then cool to 20-25° C. Filter the slurry and rinse the filter cake with 3 volumes of toluene (105 mL). Dry to a constant weight in a vacuum dryer at 50° C. to give the title compound (36.14 g, 99.2%).

$^1$H NMR (DMSO): δ=7.472 ppm (dt, 8.2 Hz, 1.9Hz, 2H); 7.112 ppm (m, 2H); 3.472 ppm (t, 7.0 Hz, 2H); 2.303 ppm (m, 5H); 2.012 ppm (m, 2H). MS: ES+=179; 157. ES-=171. Exact: 272.08.

Step 3b and 3c: Preparation of Intermediates 1-[(6-methyl-pyridin-2-yl)-2-(6-cyano-quinolin-4-yl) -ethylideneamino]-pyrrolidin-2-one and 3-(6-cyano-quinolin-4-yl)-2-(6-methyl-pyridin-2-yl) -5,6-dihydro-4H-pyrrolo[1,2-b]pyrazole Into a 3-neck, 1 L flask equipped with mechanical stirring, a Dean-Stark condenser, thermocouple and N$_2$ purge charge 2-(6-cyano-quinolin-4-yl)-1-(6-methyl-pyridin-2-yl) -ethanone (25 g, 1 equiv), 1-(amino)-2-pyrrolidinone, p-toluene sulfonate (27.3 g, 1 equiv), dimethylformamide (DMF) (150 mL, 6 vol), toluene (250 mL, 10 vol) and 2,6-lutidine (26 mL, 1 vol). Heat the mixture to reflux and periodically remove water from the trap. Monitor the reaction by HPLC or TLC analysis (5% MeOH/methylene chloride, silica). After 4 hours, most of the ketone is converted into 1-[(6-methyl-pyridin-2-yl)-2-(6-cyano-quinolin-4-yl)-ethylideneamino]-pyrrolidin-2-one as indicated by TLC.

Cool the reaction mixture to 50 to 55° C. and charge potassium carbonate (K$_2$CO$_3$) (20.42 g, 1.66 equiv) into the reaction mixture over a couple of minutes and heat the reaction mixture back up to reflux. Continue to remove the water collected in the trap and monitor the reaction by HPLC for the disappearance of hydrazone. After completion of reaction distill off most of the toluene (total distillate is 350 mL) until the reaction mixture reaches a temperature of 145° C. Cool the reaction mixture to ~30° C. and dilute with water (450 mL) and stir for 1.5 hours at room temperature (RT). Filter the formed product by filtration and rinse the cake with water 200 mL. After 1 hour under vacuum, and then dried in a vacuum oven at 70° C. to a consistent weight. The dried solid weighed 28.5 g, 93.2% yield and the purity by HPLC is 97%. The product is used as is in the next step.

$^1$H NMR (CDCl$_3$): δ=9.018 ppm (d, 4.5 Hz, 1H); 8.233 ppm (d, 8.7 Hz, 1H); 8.198 ppm (dd, 0.5 Hz, 1.8 Hz, 1H); 7.808 ppm (dd, 1.8 Hz, 8.8 Hz, 1H); 7.483-7.444 ppm (m, 2H); 7.380 ppm (d, 7.9 Hz, 1H); 6.936 ppm (d, 7.6 Hz, 1H); 4.422 ppm (t, 7.2 Hz, 2H); 2.970-2897 ppm (m, 2H); 2.776 ppm (p, 7.2 Hz, 2H); 2.065 ppm (s, 3H). MS ES+: 352.4 Exact: 351.15.

Step 4: Preparation of 2-(6-methyl-pyridin-2-yl)-3-(6-amido-quinolin-4-yl)-5,6-dihydro-4H-pyrrolo[1,2-b]pyrazole, monohydrate Slurry 3-(6-cyano-quinolin-4-yl)-2-(6-methyl-pyridin-2-yl)-5,6-dihydro-4H-pyrrolo [1,2-b]pyrazole (25.515 kg) and potassium carbonate (0.2 eq.) in 6 volumes of dimethyl sulfoxide (DMSO). Add dilute hydrogen peroxide solution [35% hydrogen peroxide (1.25 eq.) to 0.5 volumes of purified water] to the slurry over 2-3.3 hours while maintaining the temperature between 20-38° C. Monitor the reaction by HPLC (1 hour). Add sodium sulfite (0.6 eq.) to 9.1 volumes of purified water. Add the product slurry to dilute sodium sulfite solution [sodium sulfite (0.6 eq.) in 9.1 volumes of purified water] while maintaining a temperature of 20-39° C., stir this slurry for 1-2 hours to ensure all remaining hydrogen peroxide is completely neutralized. Check for peroxide. Add 1.08 vol. of 32.1% HCl Food Grade to this slurry and stir for 20-30 min. Add activated charcoal (10% by wt.) to the solution and stir for 20-40 minutes. Filter the crude product (mostly monohydrate), rinsing the cake with purified water. Add 1.05 vol. of methanol to the filtrate. Add 5.5 vol. of 2N sodium hydroxide to the filtrate while maintaining a temperature of 20-30° C. Stir the slurry for 20-30 min. Ensure pH is >8.

Filter the slurry, and rinse the cake with purified water. Suspend the wet cake in 28 vol. of a 75%/25% acetone/purified water solution. Heat this slurry to reflux (60° C.) and stir for 30-45 minutes after the product dissolves. Filter the product solution. Start the distillation, and add milled seed when the pot temperature reaches 63° C. Continue distilling until the distillate volume is 50% of the initial volume. Cool the slurry to 20-25° C. over 90 minutes. Then cool the slurry to 0-5° C. over 30-40 minutes. Stir for 2-3 hours at 0-5° C. Filter the slurry and rinse the product cake on the filter with purified water. Dry the product under vacuum at 45° C. to furnish the title compound (25.4 kg, 90%). Water content by Karl Fischer of 4.6% in monohydrate. Theory: 4.65%.

$^1$H NMR (CDCl$_3$): δ=9.0 ppm (d, 4.4 Hz, 1H); 8.23-8.19 ppm (m, 2H); 8.315 ppm (dd, 1.9 Hz, 8.9 Hz, 1H); 7.455 ppm (d, 4.4 Hz, 1H); 7.364 ppm (t, 7.7 Hz, 1H); 7.086 ppm (d, 8.0 Hz, 1H); 6.969 ppm (d, 7.7 Hz, 1H); 6.022 ppm (m, 1H); 5.497 ppm (m, 1H); 4.419 ppm (t, 7.3 Hz, 2H); 2.999 ppm (m, 2H); 2.770 ppm (p, 7.2 Hz, 7.4 Hz, 2H); 2.306 ppm (s, 3H); 1.817 ppm (m, 2H). MS ES+: 370.2; Exact: 369.16.

Alternatively, the monohydrate of the present invention can be prepared by recrystallization of 2-(6-Methyl-pyridin-2-yl)-3-[6-amido-quinolin-4-yl)-5,6-dihydro-4H-pyrrolo[1,2-b]pyrazole.

EXAMPLE 2

2-(6-Methyl-pyridin-2-yl)-3-[6-amido-quinolin-4-yl)-5,6-dihydro-4H-pyrrolo [1,2-b]pyrazole monohydrate Suspend 2-(6-methyl-pyridin-2-yl)-3-[6-amido-quinolin-4-yl)-5,6-dihydro-4H-pyrrolo [1,2-b]pyrazole in 28 vol. of a 75%/25% acetone/purified water solution. Heat this slurry to reflux (60° C.) and stir for 30-45 minutes after the product dissolves. Filter the product solution. Start the distillation, and add milled seed when the pot temperature reaches 63° C. Continue distilling until the distillate volume is 50% of the initial volume. Cool the slurry to 20-25° C. over 90 minutes. Then cool the slurry to 0-5° C. over 30-40 minutes. Stir for 2-3 hours at 0-5° C. Filter the slurry and rinse the product cake on the filter with purified water. Dry the product under vacuum at 45° C. to furnish the title compound. The reaction yield is >80%. Product purity is >98% with low total related substances.

Alternatively, the monohydrate of the present invention can be prepared by reslurrying of 2-(6-Methyl-pyridin-2-yl)-3-[6-amido-quinolin-4-yl)-5,6-dihydro-4H -pyrrolo[1,2-b]pyrazole.

EXAMPLE 3

2-(6-Methyl-pyridin-2-yl)-3-[6-amido-quinolin-4-yl)-5,6-dihydro-4H-pyrrolo [1,2-b]pyrazole monohydrate Prepare 2-(6-Methyl-pyridin-2-yl)-3-[6-amido-quinolin-4-yl-5,6-dihydro-4H -pyrrolo[1,2-b]pyrazole monohydrate by stirring the compound or active pharmaceutical ingredient (API) in 10 volumes of water at room temperature for 1-2 hours, filtering, and drying at 45° C. under vacuum.

TGF-β1 Receptor I Purification and In Vitro Kinase Reactions

For TGF-β1 Type I (RIT204D) Receptors:
The 6×-HIS tagged cytoplasmic kinase domain of each receptor was expressed and purified from Sf9 insect cell lysates as briefly described below:

Cell lysates were clarified by centrifugation and 0.45 uM filtered prior to purification by Ni/NTA affinity chromatography (Qiagen).

Chromatography Protocol:
Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1× KB (50 mM Tris pH 7.5, 150 mM NaCl, 4 mM $MgCl_2$, 1 mM NaF, 2 mM β-mercaptoethanol), elute with a linear gradient of 1× KB containing 200 mM Imidazole.

Both enzymes were approximately 90% pure and had autophosphorylation activity.

Reactions: 170-200 nM enzyme in 1× KB, compound dilution series in 1× KB/16% DMSO (20 µM to 1 nM final concentration with 4% DMSO final concentration), reactions are started by adding ATP mix (4 µM ATP/1 µCi $^{33}$P-α-ATP final concentrations) in 1× KB.

Reactions are incubated at 30° C. for 1 hour. Reactions are stopped and quantitated using standard TCA/BSA precipitation onto Millipore FB glass fiber filter plates and by liquid scintillation counting on a MicroBeta JET.

The compound disclosed herein inhibits the TGF-β1 Type I (RIT204D) receptor kinase domain with an $IC_{50}$ value of 56 nM.

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., ed., 19$^{th}$ ed., Mack Publishing Co., 1995).

The compounds of the present invention are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A crystalline 2-(6-methyl-pyridin-2-yl)-3-[6-amido-quinolin-4-yl)-5,6-dihydro -4H-pyrrolo[1,2-b]pyrazole monohydrate characterized by the X-ray powder diffraction pattern (Cu radiation, λ=1.54056 Å) comprising peaks at 9.05, 11.02, and 14.84 (2θ±0.1°).

2. The crystalline 2-(6-methyl-pyridin-2-yl)-3-[6-amido-quinolin-4-yl)-5,6-dihydro -4H-pyrrolo[1,2-b]pyrazole monohydrate of claim 1 further characterized by the X-ray powder diffraction pattern (Cu radiation, λ=1.54056 Å) comprising a peak at 11.95 (2θ±0.1°).

3. A crystalline 2-(6-methyl-pyridin-2-yl)-3-[6-amido-quinolin-4-yl)-5,6-dihydro -4H-pyrrolo[1,2-b]pyrazole monohydrate characterized by the solid state 13C nuclear magnetic resonance having a chemical shift (ppm) of 108.8, 115.6, 122.6, and 171.0 (±0.2) ppm.

4. A pharmaceutical composition comprising a compound of claim 1 and a pharmaceutically acceptable excipient, diluent, or carrier.

\* \* \* \* \*